United States Patent [19]

Schwarz et al.

[11] Patent Number: 5,563,270
[45] Date of Patent: Oct. 8, 1996

[54] PROCESS FOR THE PREPARATION OF 2-AMINO-4,6-DICHLORO-PYRIMIDINE

[75] Inventors: Franz-Thomas Schwarz, Wolfern; Johann Altreiter, Neumarkt, both of Austria

[73] Assignee: DSM Chemie Linz GmbH, Linz, Austria

[21] Appl. No.: 440,257

[22] Filed: May 12, 1995

[30] Foreign Application Priority Data

May 13, 1994 [AT] Austria ..................... 995/94

[51] Int. Cl.⁶ ........................................ C07D 239/30
[52] U.S. Cl. ................................................. 544/330
[58] Field of Search ................................... 544/330

[56] References Cited

U.S. PATENT DOCUMENTS 3,991,190  11/1976  Garzia et al. ................. 544/330
4,929,729   5/1990  Haga et al. ................... 544/330

OTHER PUBLICATIONS

Langerman et al., *Chemical Abstracts*, 46:512f (1951).
Derwent Abstracts, JO 1083-072-A (1987).

Primary Examiner—John M. Ford
Attorney, Agent, or Firm—Wenderoth, Lind & Ponack

[57] ABSTRACT

Process for the preparation of 2-amino-4,6-dichloropyrimidine by reaction of 2-amino-4,6-dihydroxypyrimidine with an excess of phosphorus oxychloride at 20 to 80° C. and in the presence of triethylamine as the acid-trapping agent.

4 Claims, No Drawings

PROCESS FOR THE PREPARATION OF 2-AMINO-4,6-DICHLORO-PYRIMIDINE

2-Amino-4,6-dichloropyrimidine (ADCP) is a known and valuable intermediate product for medicaments and agrochemicals.

A few processes for the preparation of ADCP are therefore already known from the literature. A process is thus described, for example, in U.S. Pat. No. 3,991,190, Example 1, in which 2-amino-4,6-dihydroxypyrimidine (ADHP) is reacted with an excess of phosphorusoxychloride and dimethylaniline, as an acid-trapping agent, while boiling under reflux at a temperature of about 107° C. to give ADCP. After excess phosphorusoxychloride has been distilled off, ADCP is isolated in this process by suspension in water and addition of sodium hydroxide solution until a pH of 8 to 9 is reached. In this process, however, a large number of by-products is formed and the yield of ADCP is relatively low (70%). As a proposal for improvement of the process, U.S. Pat. No. 4,929,729 describes the reaction of ADHP with phosphorusoxychloride at temperatures of 50°–100° C. in the presence of an acid-trapping agent in an additional solvent. The yield of ADCP is about 10% higher than in U.S. Pat. No. 3,991,190 (82–85%), the purity being about 91–95%. The disadvantage of this process, however, is the need for an additional solvent. Another disadvantage is that, as carried out in the examples of U.S. Pat. No. 4,929,729, to isolate the ADCP the reaction mixture has to be poured onto ice-water, after the chlorination has been carried out and the excess phosphorusoxychloride and the solvent have been separated off, and then has to be heated again to about 50° C., for which an additional expenditure of energy is necessary.

The object of the present invention was accordingly to discover a process for the preparation of 2-amino- 4,6-dichloropyrimidine which, without an additional solvent, leads to ADCP in a higher yield and higher purity than the prior art, prevents the formation of by-products and avoids the additional expenditure of energy during isolation of the ADCP.

Unexpectedly, it has been possible to achieve this object by the process according to the invention.

The present invention therefore relates to a process for the preparation of 2-amino-4,6-dichloropyrimidine, which is characterized in that 2-amino-4,6-dihydroxypyrimidine is reacted with an excess of phosphorus oxychloride at a temperature of 20° to 80° C. in the presence of triethylamine as the acid-trapping agent, and 2-amino-4,6-dichloropyrimidine is isolated. In the process according to the invention, 2-amino-4,6-dihydroxypyrimidine (ADHP) is reacted with an excess of $POCl_3$ to give 2-amino-4,6-dichloropyrimidine (ADCP). For this, the ADHP is suspended in $POCl_3$, which serves both as the reagent and as the reaction medium, which means that no additional solvent or diluent is necessary. The ease of handling the suspension is determined by the amount of $POCl_3$ employed. The molar ratio of ADHP to $POCl_3$ can be varied here, the lower limit being influenced by the stirrability of the suspension and the upper limit being influenced chiefly by economic factors. A molar ratio of ADHP to $POCl_3$ of 1:3 to 1:8, particularly preferably 1:4 to 1:6, is preferably employed. A larger excess of $POCl_3$ has no adverse effects on the reaction, and if desired can also be employed, but is not appropriate for economic reasons. The suspension thus obtained is then heated to a temperature of 20°–80° C. The more viscous the suspension to be heated, the higher the temperature should be in order to allow adequate stirrability and therefore thorough mixing. The suspension is preferably heated to 40° to 80° C., particularly preferably to 70° to 75° C.

Triethylamine is then metered into the mixture in an equivalent amount over a period of about 20 to 80 minutes, preferably 30 to 60 minutes. However, a slight excess of triethylamine can also be used, so that the molar ratio of ADHP to triethylamine is about 1:2 to 1:3, preferably 1:2.25.

When the metering has ended, stirring is continued at the reaction temperature for about a further 2 to 10 minutes, preferably 4 to 6 minutes. To isolate and work up the ADCP, the excess $POCl_3$ is distilled off in vacuo. The bottom temperature can vary here, according to the vacuum achieved, the lower limit being influenced by the stirrability of the reaction mixture and the upper limit being about 80° C. The bottom temperature is preferably kept at about 70° to 75° C. The residue is stirred into water at a temperature of about 40° to 60° C. The suspension thus obtained is stirred at about 40° to 60° C. for about a further 1.5 to 2.5 hours, and 20 to 50% strength, preferably 20% strength, NaOH is then added until a pH of about 2.5 to 4, preferably about 3, is reached.

Finally, the product which has precipitated out is filtered off, washed with water and dried in air. ADCP is obtained by the process according to the invention in yields of more than 90% and in a purity (about 99%) that are higher than in the prior art.

EXAMPLE 1

100 ml (1.12 mol) of phosphorus oxychloride and 25.4 g (0.2 mol) of 2-amino-4,6-dihydroxypyrimidine were initially introduced in succession into a 250 ml double-walled glass reactor with a stirrer, reflux condenser and thermostat heating. The suspension thus obtained was heated to 75° C. and 46 g (0.45 mol) of triethylamine were then metered in over a period of 1 hour. When the metering had ended, the mixture was stirred at 75° C. for a further 5 minutes and excess phosphorus oxychloride was then distilled off in vacuo, the bottom temperature being kept at about 75° C. The residue was stirred into 200 ml of water at a temperature of about 50° C. and stirring of the suspension thus obtained was continued at 50° C. for a further 2 hours. 20% strength NaOH was then added to the suspension until a pH of 3 was reached. The product which had precipitated out was filtered off, washed with water and dried in air.

Yield: 30.2 g (92.1%)

Content from GC: 99%

What we claim is:

1. Process for the preparation of 2-amino-4,6-dichloropyrimidine, wherein 2-amino-4,6-dihydroxypyrimidine is reacted with an excess of phosphorus oxychloride at a temperature of 20° to 80° C. in the presence of triethylamine as the acid-trapping agent, but without an additional solvent, and 2-amino-4,6-dichloropyrimidine being isolated by removing excess phosphorus oxychloride, suspending the residue in water of 40° to 60° C., adding NaOH until a pH of about 2.5 to 4 is reached and filtering off 2-amino-4,6-dichloropyrimidine.

2. Process according to claim 1, wherein the 2-amino-4,6-dihydroxypyrimidine and phosphorus oxychloride are employed in a molar ratio of 1 : 3 to 1: 8.

3. Process according to claim 1, wherein the triethylamine is employed in a molar ratio to the 2-amino-4,6- dihydroxypyrimidine of 2: 1 to 3: 1.

4. Process according to claim 1, wherein, to isolate the 2-amino-4,6-dichloropyrimidine, excess phosphorus oxychloride is distilled off in vacuo, the residue is-suspended in water at 40°–60° C., after stirring for 1.5 to 2.5 hours, 20–50% strength NaOH is added to the suspension thus obtained until a pH of about 2.5 to 4 is reached, after which the 2-amino-4,6-dichloropyrimidine which has precipitated out is filtered off, washed with water and dried in air.

* * * * *